(12) United States Patent
Varadhan et al.

(10) Patent No.: US 11,806,012 B2
(45) Date of Patent: Nov. 7, 2023

(54) SURGICAL STAPLING DEVICE WITH KNIFE BLADE LOCK

(71) Applicant: Covidien LP, Mansfield, MA (US)

(72) Inventors: Sridharan Varadhan, Shanghai (CN); Ping Ren, Shanghai (CN)

(73) Assignee: Covidien LP, Mansfield, MA (US)

( * ) Notice: Subject to any disclaimer, the term of this patent is extended or adjusted under 35 U.S.C. 154(b) by 283 days.

(21) Appl. No.: 17/260,389

(22) PCT Filed: Nov. 1, 2019

(86) PCT No.: PCT/CN2019/115019
§ 371 (c)(1),
(2) Date: Jan. 14, 2021

(87) PCT Pub. No.: WO2021/081984
PCT Pub. Date: May 6, 2021

(65) Prior Publication Data
US 2022/0000475 A1    Jan. 6, 2022

(51) Int. Cl.
*A61B 17/072* (2006.01)
*A61B 90/00* (2016.01)

(52) U.S. Cl.
CPC .. *A61B 17/072* (2013.01); *A61B 2017/07221* (2013.01); *A61B 2017/07271* (2013.01); *A61B 2017/07285* (2013.01); *A61B 2090/038* (2016.02)

(58) Field of Classification Search
CPC ........ A61B 17/072; A61B 2017/07221; A61B 2017/07271; A61B 2017/07285

USPC .................................................... 227/175.4
See application file for complete search history.

(56) References Cited

U.S. PATENT DOCUMENTS

| | | |
|---|---|---|
| 1,158,111 A | 10/1915 | Ahlheim |
| 2,891,250 A | 6/1959 | Hirata |
| 3,080,564 A | 3/1963 | Strekopitov et al. |
| 3,252,643 A | 5/1966 | Strekopov et al. |
| 3,269,630 A | 8/1966 | Fleischer |
| 3,275,211 A | 9/1966 | Hirsch et al. |
| 3,315,863 A | 4/1967 | O'Dea |
| 3,494,533 A | 2/1970 | Green et al. |
| 3,589,589 A | 6/1971 | Akopov |
| 3,692,224 A | 9/1972 | Astafiev et al. |
| 3,795,034 A | 3/1974 | Strekopytov et al. |

(Continued)

FOREIGN PATENT DOCUMENTS

| | | |
|---|---|---|
| CN | 1669534 A | 9/2005 |
| CN | 104224260 A | 12/2014 |

(Continued)

OTHER PUBLICATIONS

International Search Report dated Aug. 10, 2020, issued in corresponding international application No. PCT/CN2019/115019, 5 pages.

(Continued)

*Primary Examiner* — Michelle Lopez
(74) *Attorney, Agent, or Firm* — Carter, DeLuca & Farrell LLP

(57) ABSTRACT

A surgical stapling device includes a cartridge assembly including a cartridge body, a staple pusher, a knife assembly, and a locking device. The locking device is configured to prevent readvancement of the knife assembly.

22 Claims, 10 Drawing Sheets

(56) References Cited

U.S. PATENT DOCUMENTS

| | | |
|---|---|---|
| 3,822,818 A | 7/1974 | Strekopytov et al. |
| 3,935,981 A | 2/1976 | Akopov et al. |
| 3,949,923 A | 4/1976 | Akopov et al. |
| 4,047,654 A | 9/1977 | Alvarado |
| 4,216,891 A | 8/1980 | Behlke |
| 4,244,372 A | 1/1981 | Kapitanov et al. |
| 4,296,881 A | 10/1981 | Lee |
| 4,305,539 A | 12/1981 | Korolkov et al. |
| 4,354,628 A | 10/1982 | Green |
| 4,378,901 A | 4/1983 | Akopov et al. |
| 4,383,634 A | 5/1983 | Green |
| 4,402,444 A | 9/1983 | Green |
| 4,415,112 A | 11/1983 | Green |
| D273,513 S | 4/1984 | Spreckelmeier |
| 4,442,964 A | 4/1984 | Becht |
| 4,470,533 A | 9/1984 | Schuler |
| 4,475,679 A | 10/1984 | Fleury, Jr. |
| 4,485,811 A | 12/1984 | Chernousov et al. |
| 4,506,670 A | 3/1985 | Crossley |
| 4,506,671 A | 3/1985 | Green |
| 4,508,253 A | 4/1985 | Green |
| 4,522,327 A | 6/1985 | Korthoff et al. |
| 4,527,724 A | 7/1985 | Chow et al. |
| 4,530,453 A | 7/1985 | Green |
| 4,550,870 A | 11/1985 | Krumme et al. |
| 4,566,620 A | 1/1986 | Green et al. |
| 4,568,009 A | 2/1986 | Green |
| 4,573,622 A | 3/1986 | Green et al. |
| 4,580,712 A | 4/1986 | Green |
| 4,585,153 A | 4/1986 | Failla et al. |
| 4,589,582 A | 5/1986 | Bilotti |
| 4,602,634 A | 7/1986 | Barkley |
| 4,605,001 A | 8/1986 | Rothfuss et al. |
| 4,605,004 A | 8/1986 | Di Giovanni et al. |
| 4,606,344 A | 8/1986 | Di Giovanni |
| 4,606,345 A | 8/1986 | Dorband et al. |
| 4,607,636 A | 8/1986 | Kula et al. |
| 4,612,933 A | 9/1986 | Brinkerhoff et al. |
| 4,617,928 A | 10/1986 | Alfranca |
| 4,632,290 A | 12/1986 | Green et al. |
| 4,665,916 A | 5/1987 | Green |
| 4,684,051 A | 8/1987 | Akopov et al. |
| 4,714,187 A | 12/1987 | Green |
| 4,715,520 A | 12/1987 | Roehr, Jr. et al. |
| 4,728,020 A | 3/1988 | Green et al. |
| 4,767,044 A | 8/1988 | Green |
| 4,788,978 A | 12/1988 | Strekopytov et al. |
| 4,802,614 A | 2/1989 | Green et al. |
| 4,805,823 A | 2/1989 | Rothfuss |
| 4,819,853 A | 4/1989 | Green |
| 4,848,637 A | 7/1989 | Pruitt |
| 4,869,414 A | 9/1989 | Green et al. |
| 4,881,544 A | 11/1989 | Green et al. |
| 4,881,545 A | 11/1989 | Isaacs et al. |
| 4,915,100 A | 4/1990 | Green |
| 4,930,503 A | 6/1990 | Pruitt |
| 4,938,408 A | 7/1990 | Bedi et al. |
| 4,941,623 A | 7/1990 | Pruitt |
| 4,951,861 A | 8/1990 | Schulze et al. |
| 4,964,559 A | 10/1990 | Deniega et al. |
| 5,005,754 A | 4/1991 | Van Overloop |
| 5,018,657 A | 5/1991 | Pedlick et al. |
| 5,071,052 A | 12/1991 | Rodak et al. |
| 5,100,042 A | 3/1992 | Gravener et al. |
| 5,116,349 A | 5/1992 | Aranyi |
| 5,137,198 A | 8/1992 | Nobis et al. |
| 5,172,845 A | 12/1992 | Tejeiro |
| 5,190,203 A | 3/1993 | Rodak |
| 5,219,111 A | 6/1993 | Bilotti et al. |
| 5,240,163 A | 8/1993 | Stein et al. |
| 5,344,060 A | 9/1994 | Gravener et al. |
| 5,368,599 A | 11/1994 | Hirsch et al. |
| 5,405,073 A | 4/1995 | Porter |
| 5,413,267 A | 5/1995 | Solyntjes et al. |
| 5,439,155 A | 8/1995 | Viola |
| 5,452,836 A | 9/1995 | Huitema et al. |
| 5,458,279 A | 10/1995 | Plyley |
| 5,462,215 A | 10/1995 | Viola et al. |
| 5,464,144 A | 11/1995 | Guy et al. |
| 5,465,894 A | 11/1995 | Clark et al. |
| 5,470,006 A | 11/1995 | Rodak |
| 5,470,008 A | 11/1995 | Rodak |
| 5,470,009 A | 11/1995 | Rodak |
| 5,497,934 A | 3/1996 | Brady et al. |
| 5,503,320 A | 4/1996 | Webster et al. |
| 5,509,596 A | 4/1996 | Green et al. |
| 5,542,594 A | 8/1996 | McKean et al. |
| 5,547,117 A | 8/1996 | Hamblin et al. |
| 5,558,266 A | 9/1996 | Green et al. |
| 5,579,978 A | 12/1996 | Green et al. |
| 5,580,067 A | 12/1996 | Hamblin et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,615,820 A | 4/1997 | Viola |
| 5,641,111 A | 6/1997 | Ahrens et al. |
| 5,678,748 A | 10/1997 | Plyley et al. |
| 5,697,543 A | 12/1997 | Burdorff |
| 5,706,997 A | 1/1998 | Green et al. |
| 5,706,998 A | 1/1998 | Plyley et al. |
| 5,732,871 A | 3/1998 | Clark et al. |
| 5,735,445 A | 4/1998 | Vidal et al. |
| 5,794,834 A | 8/1998 | Hamblin et al. |
| 5,810,240 A | 9/1998 | Robertson |
| 5,855,311 A | 1/1999 | Hamblin et al. |
| 5,878,937 A | 3/1999 | Green et al. |
| 5,893,506 A | 4/1999 | Powell |
| 5,894,979 A | 4/1999 | Powell |
| 5,964,394 A | 10/1999 | Robertson |
| 6,045,560 A | 4/2000 | McKean et al. |
| 6,638,285 B2 | 10/2003 | Gabbay |
| 6,805,273 B2 | 10/2004 | Bilotti et al. |
| 6,817,508 B1 | 11/2004 | Racenet et al. |
| 6,988,650 B2 | 1/2006 | Schwemberger et al. |
| 7,070,083 B2 | 7/2006 | Jankowski |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,210,609 B2 | 5/2007 | Leiboff et al. |
| 7,237,708 B1 | 7/2007 | Guy et al. |
| 7,275,674 B2 | 10/2007 | Racenet et al. |
| RE40,237 E | 4/2008 | Bilotti et al. |
| 7,407,076 B2 | 8/2008 | Racenet et al. |
| 7,431,190 B2 | 10/2008 | Hoffman |
| 7,522,854 B2 | 4/2009 | Kinouchi et al. |
| 7,549,563 B2 | 6/2009 | Mather et al. |
| 7,568,605 B2 | 8/2009 | Kruszynski |
| 7,641,092 B2 | 1/2010 | Kruszynski et al. |
| 7,717,312 B2 | 5/2010 | Beetel |
| 7,731,073 B2 | 6/2010 | Wixey et al. |
| 7,735,704 B2 | 6/2010 | Bilotti |
| 7,766,207 B2 | 8/2010 | Mather et al. |
| 7,810,690 B2 | 10/2010 | Bilotti et al. |
| 7,886,953 B2 | 2/2011 | Schwemberger et al. |
| 8,016,176 B2 | 9/2011 | Kasvikis et al. |
| 8,029,520 B2 | 10/2011 | Korvick et al. |
| 8,033,439 B2 | 10/2011 | Racenet et al. |
| 8,070,038 B2 | 12/2011 | Kostrzewski |
| 8,231,041 B2 | 7/2012 | Marczyk et al. |
| 8,292,904 B2 | 10/2012 | Popovic et al. |
| 8,360,296 B2 | 1/2013 | Zingman |
| 8,424,738 B2 | 4/2013 | Kasvikis |
| 8,499,994 B2 | 8/2013 | D'Arcangelo |
| 8,596,515 B2 | 12/2013 | Okoniewski |
| 8,627,994 B2 | 1/2014 | Zemlok et al. |
| 8,646,673 B2 | 2/2014 | Bilotti et al. |
| 8,757,467 B2 | 6/2014 | Racenet et al. |
| 8,936,185 B2 | 1/2015 | Racenet et al. |
| 8,955,732 B2 | 2/2015 | Zemlok et al. |
| 8,967,446 B2 | 3/2015 | Beardsley et al. |
| 9,022,273 B1 | 5/2015 | Marczyk et al. |

(56) References Cited

U.S. PATENT DOCUMENTS

| | | |
|---|---|---|
| 9,125,651 B2 | 9/2015 | Mandakolathur Vasudevan et al. |
| 9,192,382 B2 | 11/2015 | Kostrzewski |
| 9,814,460 B2 | 11/2017 | Kimsey et al. |
| 9,888,923 B2 | 2/2018 | Chen et al. |
| 10,194,913 B2 | 2/2019 | Nalagatla et al. |
| 2004/0164123 A1 | 8/2004 | Racenet et al. |
| 2005/0143759 A1* | 6/2005 | Kelly .................. A61B 17/072 |
| | | 606/139 |
| 2005/0247752 A1 | 11/2005 | Kelly et al. |
| 2005/0247753 A1 | 11/2005 | Kelly et al. |
| 2006/0163312 A1 | 7/2006 | Viola et al. |
| 2007/0039996 A1* | 2/2007 | Mather ................ A61B 17/072 |
| | | 227/176.1 |
| 2007/0187456 A1 | 8/2007 | Viola et al. |
| 2010/0048988 A1 | 2/2010 | Pastorelli et al. |
| 2013/0206813 A1 | 8/2013 | Nalagatla |
| 2016/0249914 A1 | 9/2016 | Zhang et al. |
| 2017/0014134 A1 | 1/2017 | Chen et al. |
| 2017/0027571 A1 | 2/2017 | Nalagatla et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0189021 A1* | 7/2017 | Kimsey ................ A61B 17/072 |
| 2017/0189024 A1* | 7/2017 | Adams ................ A61B 17/068 |
| 2019/0000455 A1 | 1/2019 | Adams et al. |

FOREIGN PATENT DOCUMENTS

| | | |
|---|---|---|
| CN | 104921770 A | 9/2015 |
| CN | 107928733 A | 4/2018 |
| CN | 108113722 A | 6/2018 |
| CN | 108125697 A | 6/2018 |
| EP | 3769698 A2 | 1/2021 |
| EP | 3815626 A1 | 5/2021 |
| WO | WO-2012177409 A1 * | 12/2012 ........... A61B 17/072 |

OTHER PUBLICATIONS

Written Opinion of the International Searching Authority dated Aug. 10, 2020, issued in corresponding international application No. PCT/CN2019/115019, 4 pages.

Extended European Search Report dated May 25, 2023, issued in corresponding EP Appln. No. 19950859, 8 pages.

* cited by examiner

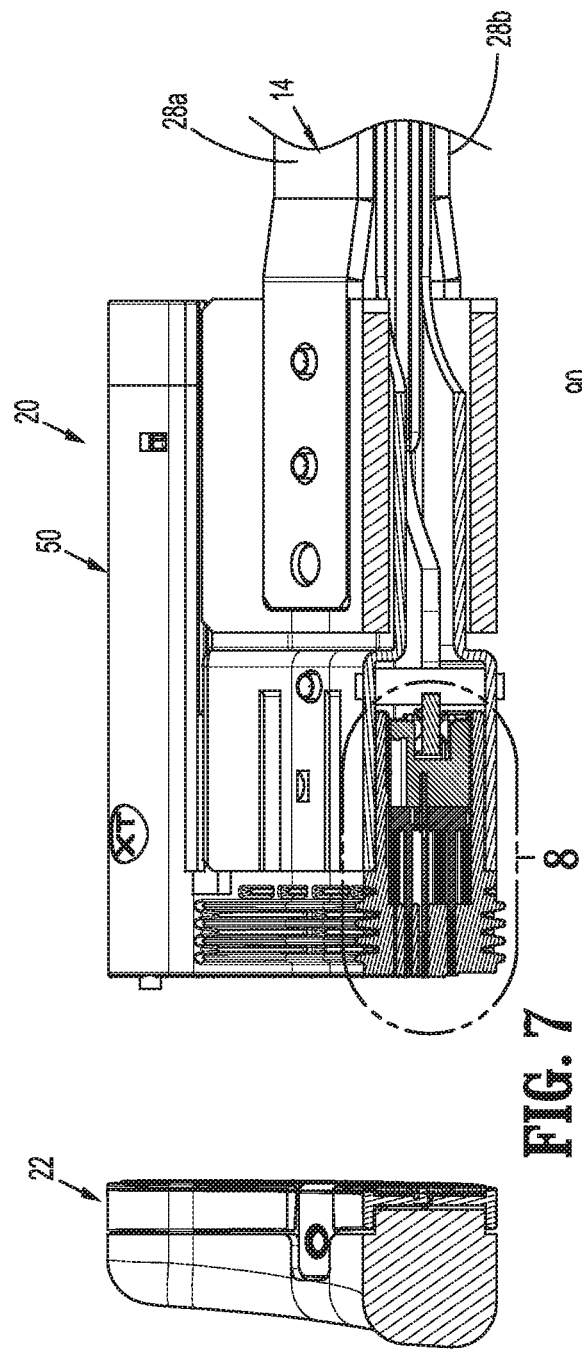
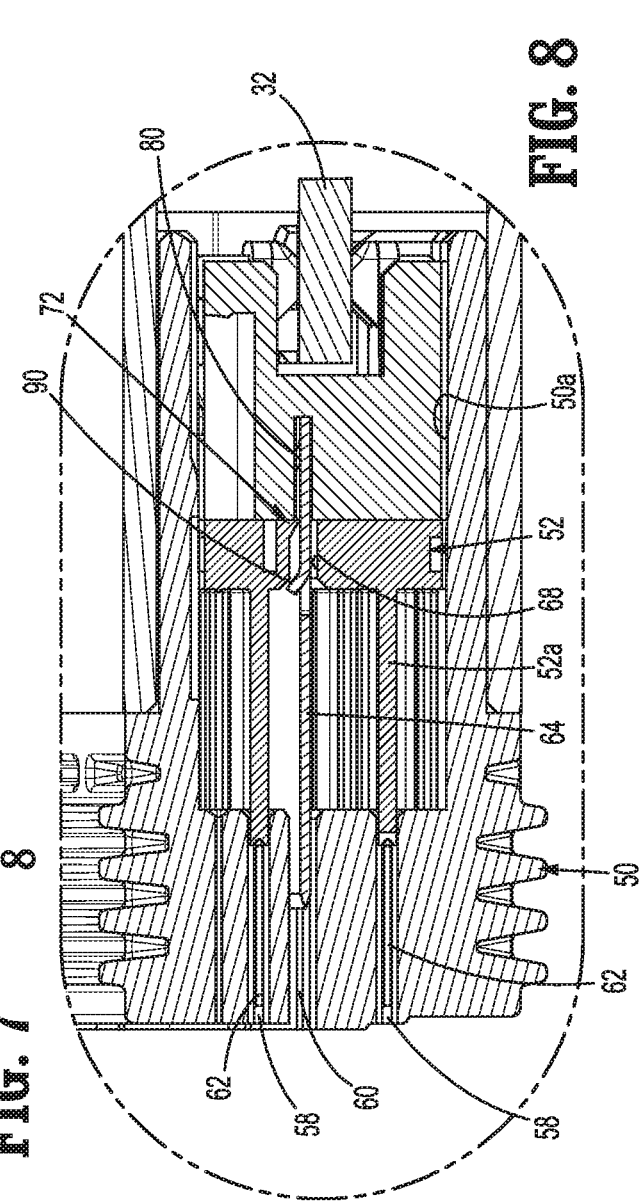

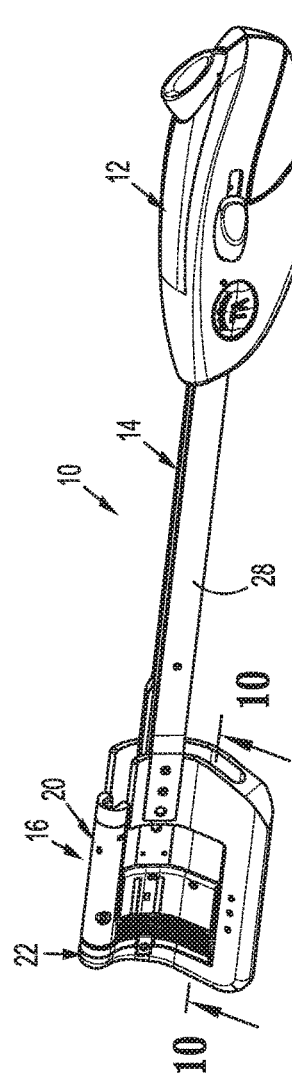
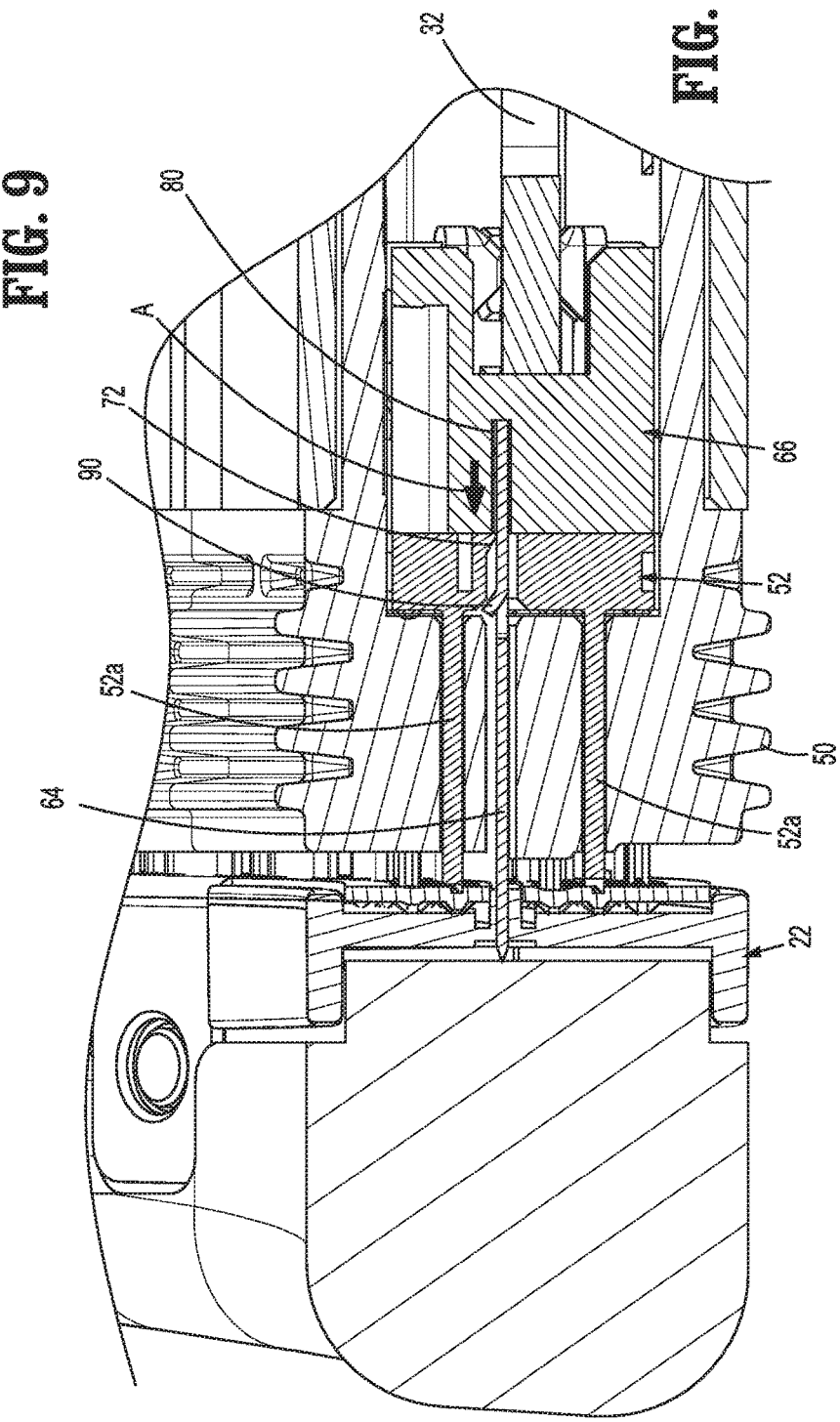
FIG. 9
FIG. 10

SURGICAL STAPLING DEVICE WITH KNIFE BLADE LOCK

CROSS-REFERENCE TO RELATED APPLICATION

This application is a National Stage Application of PCT Application Serial No.: PCT/CN2019/115019 under 35 U.S.C. § 371(a), filed Nov. 1, 2019, the disclosure of which is incorporated by reference herein it its entirety.

FIELD

The technology is generally related to surgical stapling devices and, more particularly, to surgical stapling devices with retractable knife assemblies.

BACKGROUND

Surgical stapling devices for applying rows of staples through compressed living tissue are known in the art and are commonly used for closure of tissue or organs prior to transection or resection of the tissue and for occlusion of the organs during thoracic or abdominal procedures. Such stapling devices sometimes include a knife for transecting or resecting the tissue or organs simultaneously with application of the staples to the tissue.

Typically, the stapling devices include a tool assembly including an anvil assembly and a cartridge assembly, a drive member or pusher, and an approximation assembly for moving the tool assembly between spaced and clamped positions. The tool assembly is available in a variety of configurations including linear, curved, and circular. In addition, the tool assembly is available in a variety of orientations in relation to a longitudinal axis of the stapling device including parallel orientations and transverse orientations.

In transverse type stapling devices, the cartridge assembly may include cartridge body and a knife assembly including a blade having a cutting edge. The knife assembly can be advanced from within the cartridge body when the stapling device is actuated to transect or resect the tissue. After the stapling device is actuated, the knife assembly is retracted to a position in which the cutting edge of the blade is shielded to protect a clinician from injury.

A continuing need exists for a stapling device including a simple lock design capable of retaining the knife assembly in a shielded position within the cartridge body.

SUMMARY

Aspects of this disclosure generally relate to surgical stapling devices including a cartridge assembly having a retractable knife assembly. In aspects of the disclosure, the cartridge assembly includes locking device on the knife assembly to prevent readvancement of the knife assembly.

One aspect of the disclosure is directed to a stapling device including a handle assembly, an elongate body, an approximation assembly, a tool assembly, and a locking device. The handle assembly includes a stationary handle and a trigger that is movable in relation to the stationary handle. The elongate body extends distally from the handle assembly, defines a longitudinal axis, and has a distal portion and a proximal portion. The approximation assembly extends from the handle assembly along the elongate body and includes a clamp slide assembly having a distal support portion. The clamp slide assembly is movable along the elongate body between retracted and advanced positions. The tool assembly is supported on the distal portion of the elongate body and includes an anvil assembly and a cartridge assembly. The cartridge assembly is releasably supported on the distal support portion of the clamp slide assembly and is movable in relation to the anvil assembly between spaced and clamped positions in response to movement of the clamp slide assembly between the retracted and advanced positions. The cartridge assembly includes a cartridge body, a knife assembly, and a staple pusher. The knife assembly is positioned within the cartridge body at a position proximally of the staple pusher and is movable between retracted and advanced positions in response to actuation of the handle assembly. The staple pusher is positioned within the staple cartridge distally of the knife assembly such that movement of the knife assembly from its retracted position to its advanced position moves the staple pusher from its retracted position to its advanced position. The locking device is supported on the cartridge assembly and includes a stop member supported on one of the knife assembly and the staple pusher and a locking projection supported on the other of the knife assembly and the staple pusher. The locking projection is movable from a first position permitting advancement of the knife assembly to a second position obstructing advancement of the knife assembly in response to movement of the knife assembly from its advanced position back to its retracted position.

In aspects of the disclosure, the knife assembly includes a knife blade and a knife holder and the knife blade is secured to the knife holder and defines a cutting edge.

In some aspects of the disclosure, the cartridge assembly and the anvil assembly define axes that are transverse to the longitudinal axis of the elongate body.

In some aspects of the disclosure, the cartridge assembly and the anvil assembly are curved along their longitudinal axes.

In certain aspects of the disclosure, the staple pusher defines a knife slot and the knife blade is movably positioned within the knife slot.

In aspects of the disclosure, the stop member is formed on the staple pusher and the locking projection is formed on the knife blade, wherein the locking projection extends into the knife slot of the staple pusher.

In some aspects of the disclosure, the stop member includes a tapered distal face and a proximally facing stop surface that extends in a direction transverse to the longitudinal axis of the elongate body.

In aspects of the disclosure, the stop member is deformable from an undeformed condition to a deformed condition upon engagement with the locking projection to facilitate movement of the locking projection from a position distal of the stop surface to a position proximal of the stop surface.

In certain aspects of the disclosure, the locking projection includes a tab that extends from the knife blade and is aligned with the stop member within the knife slot.

In aspects of the disclosure, the locking projection includes a tapered proximal face that is aligned with the tapered distal face of the stop member when the staple pusher and the knife assembly are in their retracted positions.

In some aspects of the disclosure, the stop member is formed on the knife holder of the knife assembly and the locking projection is formed on the staple pusher.

In certain aspects of the disclosure, the stop member includes a proximally facing angled wall and a distally facing stop surface, wherein the distally facing stop surface extends in a direction perpendicular to the longitudinal axis of the elongate body.

In aspects of the disclosure, the locking projection includes a resilient leaf spring supported on the staple pusher, wherein the resilient leaf spring has a proximal end and is movable from a deformed condition to a non-deformed condition in response to movement of the knife assembly from its advanced position to its retracted position.

In some aspects of the disclosure, when the staple pusher and the knife assembly are in their retracted positions, the resilient leaf spring is positioned on the angled wall of the stop member in the deformed condition with the proximal end of the resilient leaf spring positioned proximally of the stop surface.

In certain aspects of the disclosure, when the knife assembly is in its retracted position and the staple pusher is in its advanced position, the proximal end of the resilient leaf spring is positioned distally of the stop surface.

Another aspect of the disclosure is directed to a cartridge assembly including a cartridge body, a knife assembly, a staple pusher, and a locking device. The knife assembly is positioned within the cartridge body and is movable between retracted and advanced positions. The staple pusher is positioned within the cartridge body distally of the knife assembly such that movement of the knife assembly from its retracted position to its advanced position moves the staple pusher from a retracted position to an advanced position. The locking device includes a stop member supported on one of the knife assembly and the staple pusher and a locking projection supported on the other of the knife assembly and the staple pusher. The locking projection is movable in response to movement of the knife assembly from its advanced position back to its retracted position from a first position permitting advancement of the knife assembly to a second position obstructing advancement of the knife assembly.

Other features of the disclosure will be appreciated from the following description.

BRIEF DESCRIPTION OF DRAWINGS

Various aspects of the disclosure are described herein below with reference to the drawings, wherein:

FIG. 7 is a cross-sectional view taken along section lines 7-7 of FIG. 1;

FIG. 8 is an enlarged view of the indicated area of detail shown in FIG. 7;

FIG. 9 is a side perspective view of the stapling device shown in FIG. 1 in the clamped and fired position with the knife assembly in an advanced position;

FIG. 10 is a cross-sectional view taken along section lines 10-10 of FIG. 9;

DETAILED DESCRIPTION

Figure 1:
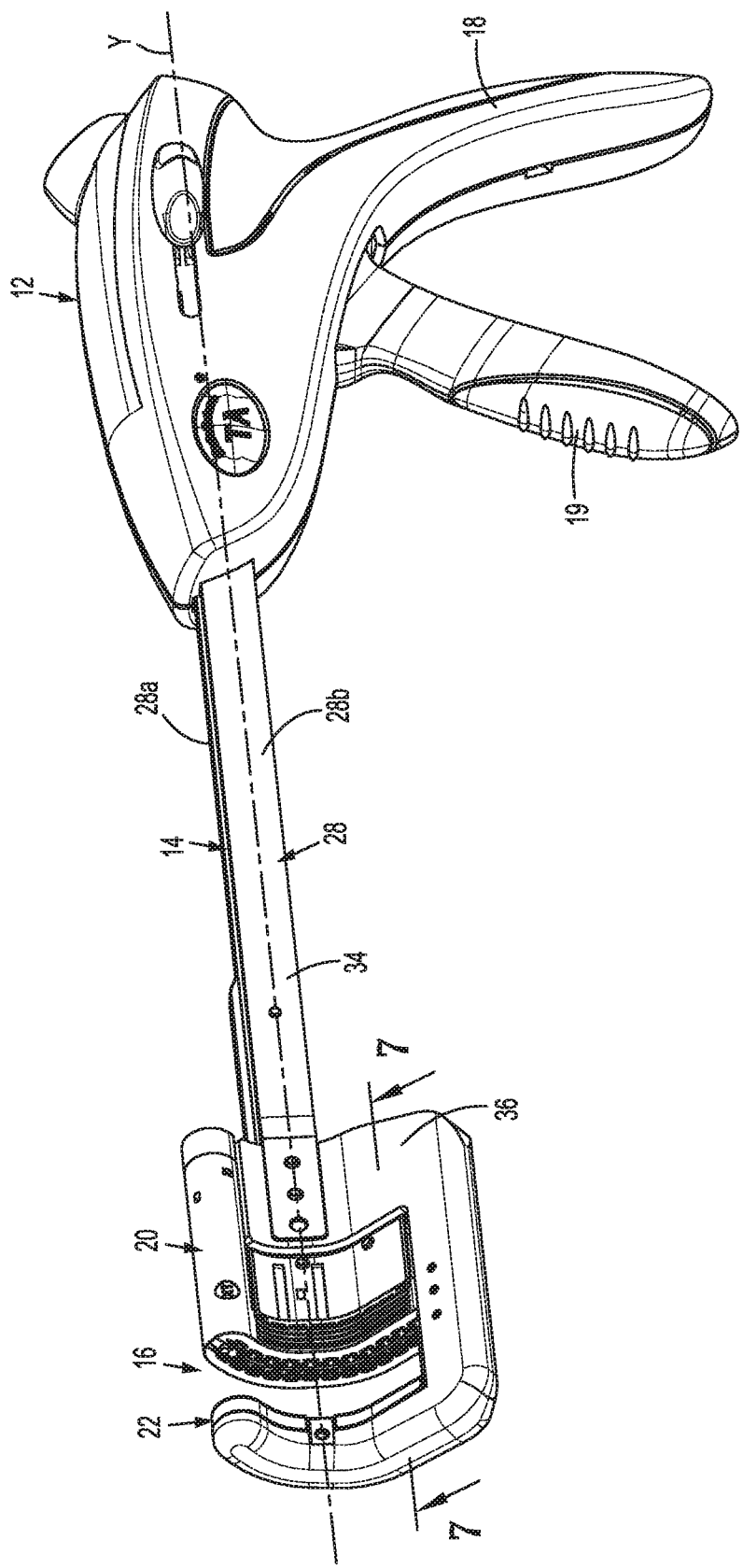
FIG. 1 is a side perspective view of a stapling device including aspects of the disclosure with the stapling device in an unclamped position.

The disclosed device will now be described in detail with reference to the drawings in which like reference numerals designate identical or corresponding elements in each of the several views. However, it is to be understood that the disclosed aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

The disclosed surgical stapling device includes a cartridge assembly having a knife assembly including a knife blade having a cutting edge, and a locking device. The knife assembly is movable from a retracted position shielded within a body of the cartridge assembly and an advanced position extending from the body of the cartridge assembly to transect or resect body tissue. After the stapling device is fired, the knife assembly is movable back to the retracted position to shield the cutting edge of the knife blade within the body of the cartridge assembly. The locking device is supported on the cartridge assembly and retains the knife blade in the retracted position after the stapling device is fired to prevent injury to a clinician during disposal of the cartridge assembly.

FIG. 1 illustrates the disclosed surgical stapling device shown generally as stapling device 10. The stapling device 10 includes a handle assembly 12, an elongate body 14 that defines a longitudinal axis "Y", and a tool assembly 16. The handle assembly 12 includes a stationary handle 18 and a trigger 19 that is movable in relation to the stationary handle 18 to actuate the tool assembly 16. The tool assembly 16 includes a staple cartridge assembly 20 and an anvil assembly 22 that define axes that are transverse to the longitudinal axis "Y" of the elongate body 14. The cartridge assembly 20 is supported on a distal end portion of the elongate body 14 and is movable in relation to the anvil assembly 22 between an unclamped position (FIG. 1) and a clamped position (FIG. 9). In the clamped position, the cartridge assembly 20 is in juxtaposed alignment with the anvil assembly 22. In some aspects of the disclosure, the cartridge assembly 20 and the anvil assembly 22 are curved to facilitate access to certain anatomical regions of the human body.

Figure 2:
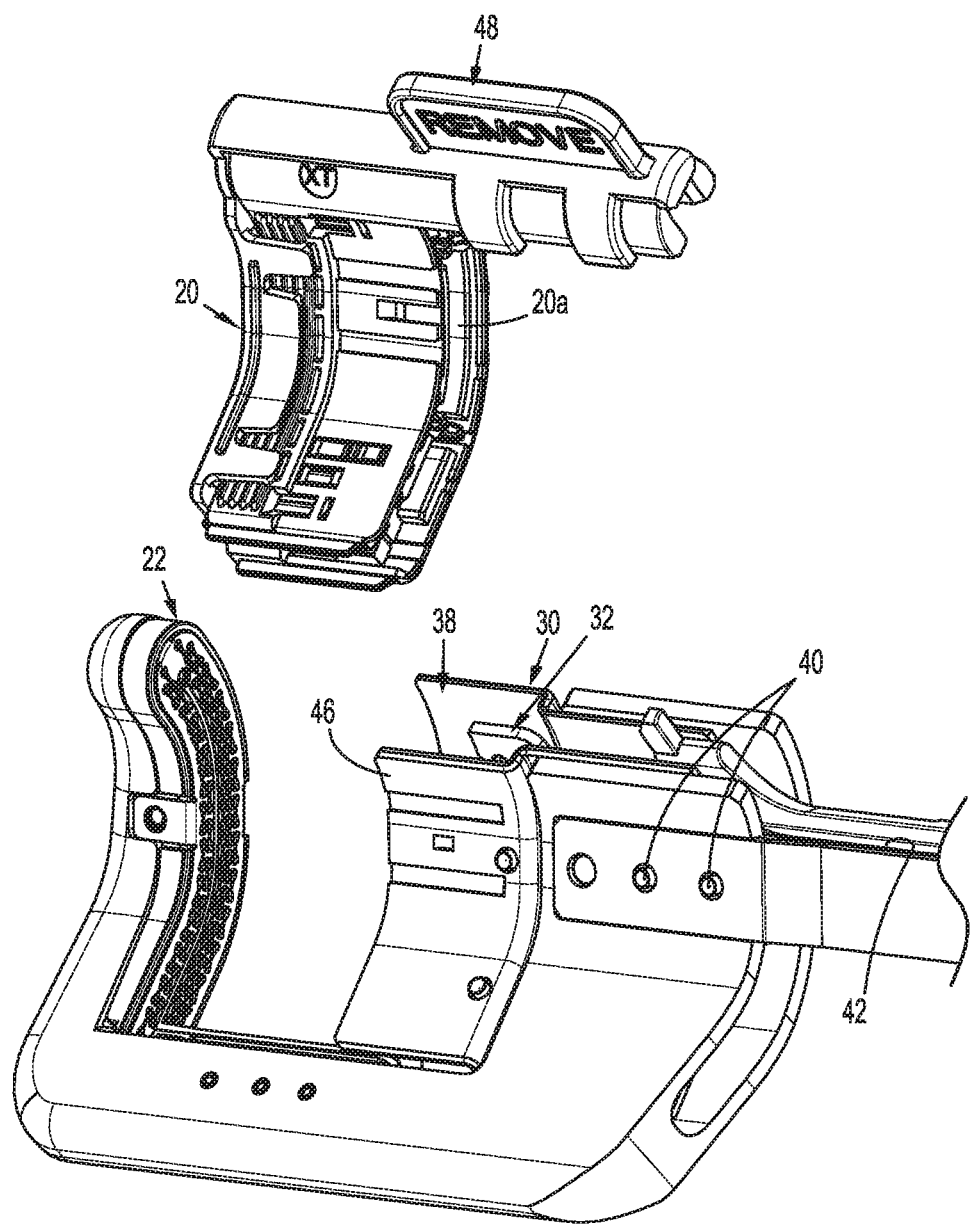
FIG. 2 is a side perspective of a distal portion of the stapling device shown in FIG. 1 illustrating a clamp slide assembly and a tool assembly with a cartridge assembly of the tool assembly separated from the clamp slide assembly.

FIGS. 1 and 2 illustrate a frame assembly 28 of the stapling device 10 that includes a proximal portion (not shown) that forms a portion of the handle assembly 12, a central portion 34 that forms a portion of the elongate body 14, and a distal portion 36 that forms a portion of the tool assembly 16. The frame assembly 28 includes frame members 28a and 28b that are secured together with, e.g., rivets 40 (FIG. 2), in spaced relation to each other to define a channel 42 (FIG. 2) between the frame members 28a and 28b. Alternately, the frame assembly 28 can be of unitary construction.

The stapling device 10 includes an approximation mechanism 30 and a thrust bar 32 (FIG. 2). The approximation mechanism 30 includes a clamp slide assembly 38 that is supported within the channel 42 of the frame assembly 28 for movement between retracted and advanced positions. The clamp slide assembly 38 includes a distal support portion 46 that supports the cartridge assembly 20 when the cartridge assembly 20 is engaged with the clamp slide assembly 38. In aspects of the disclosure, the distal support portion 46 of the clamp slide assembly 38 defines a pocket that receives the cartridge assembly 20. Alternately, the distal support portion 46 of the clamp slide assembly 38 can be received within a cartridge body 20a of the cartridge assembly 20.

The approximation mechanism 30 is actuated to move the stapling device 10 between its unclamped and clamped positions. In the clamped position of the stapling device 10, the cartridge assembly 22 is positioned in juxtaposed alignment with the anvil assembly 22. The thrust bar 32 (FIG. 2) is provided to facilitate firing of staples (not shown) from the cartridge assembly 20 into the anvil assembly 22. For a more detailed description of the handle assembly 12 and operation of the thrust bar 44, see U.S. Pat. No. 6,817,508 ("the '508 patent").

In some stapling devices, a shipping wedge 48 (FIG. 2) is secured to the cartridge assembly 20. The shipping wedge 48 prevents inadvertent advancement of the internal components of the cartridge assembly 20 to retain the cartridge assembly 20 in an operation ready position. The shipping wedge 48 is removed by the clinician prior to securement of the cartridge assembly 20 to the stapling device 10.

Figure 3:
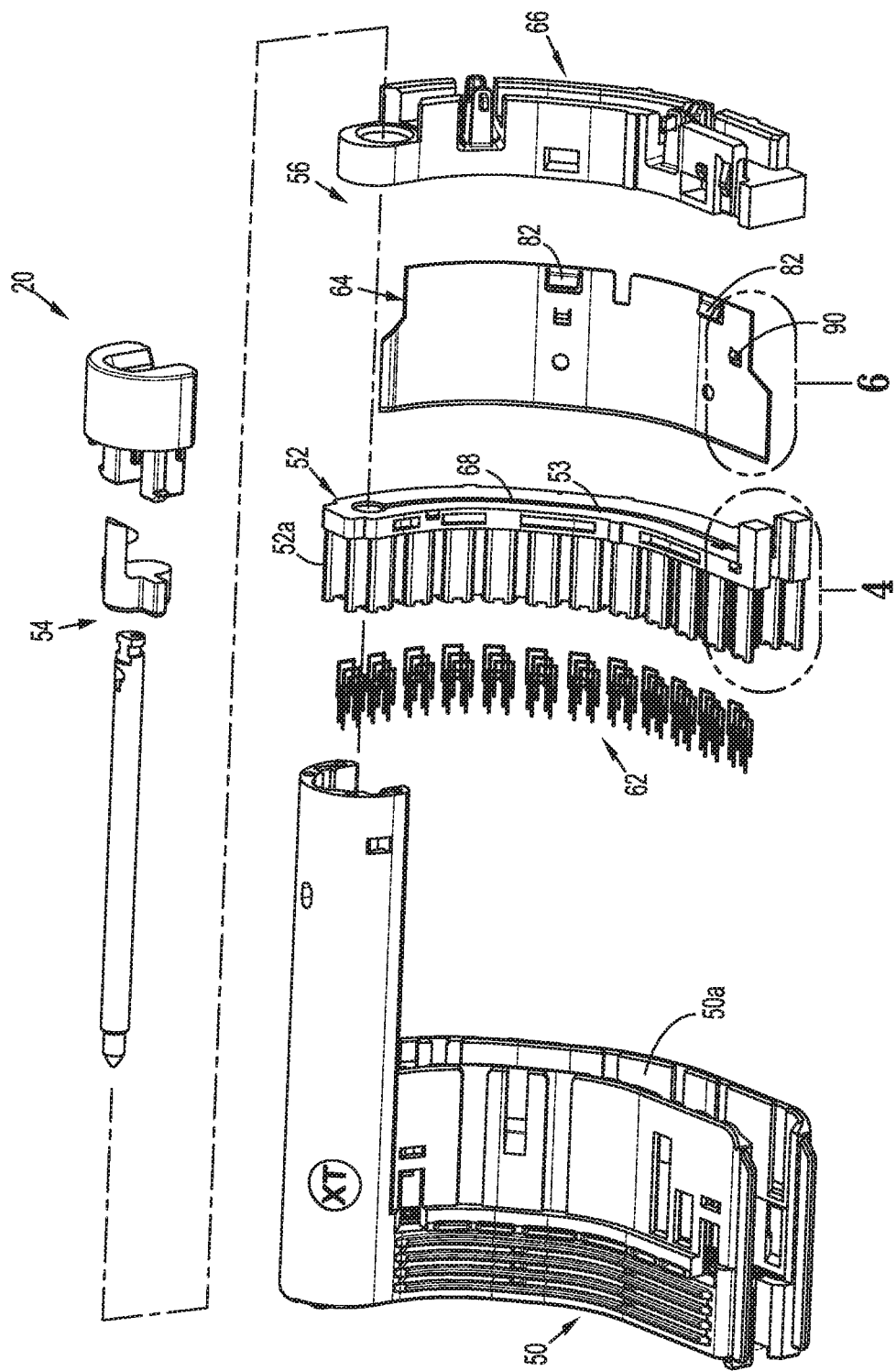
FIG. 3 is a side perspective exploded view of the cartridge assembly shown in FIG. 2.

FIG. 3 illustrates the cartridge assembly 20 which includes a cartridge body 50, a staple pusher 52, an alignment pin assembly 54, and a knife assembly 56. The cartridge body 50 defines rows of staple pockets 58 (FIG. 8) and a knife slot 60 that is positioned between the rows of staple pockets 58. Each of the staple pockets 58 supports a staple 62. The cartridge body 50 also defines a cavity 50a that receives the staple pusher 52 and the knife assembly 56. The cavity 50a defined by the cartridge body 50 is dimensioned to allow for movement of the staple pusher 52 and knife assembly 56 from retracted positions (FIG. 8) to advanced positions (FIG. 10) within the cavity 50a. For a more detailed description of the alignment pin assembly 54 and its operation, see the '508 patent.

The staple pusher 52 includes a plurality of fingers 52a (FIG. 3) that extend distally from within the cavity 50a of the cartridge body 50 into the respective staple pockets 58 (FIG. 8) of the cartridge body 50. The staple pusher 52 defines a knife slot 68 that extends through the staple pusher 52 and is aligned with the knife slot 60 in the cartridge body 50 (FIG. 8). When the staple pusher 52 is moved within the cavity 50a of the cartridge body 50 from its retracted position to its advanced position, the fingers 52a of the staple pusher 52 are advanced through the staple pockets 58 (FIG. 8) to eject the staples 62 from the cartridge body 50.

The knife assembly 56 includes a knife blade 64 and a knife holder 66. The knife holder 66 is supported within the cavity 50a of the cartridge body 50 at a location proximal of the staple pusher 52. When the knife holder 66 is moved from its retracted position (FIG. 8) towards its advanced position (FIG. 10), the knife holder 66 moves into engagement with the staple pusher 52 to advance the staple pusher 52 from its retracted position to its advanced position. As shown in FIG. 8, the knife blade 64 is coupled to the knife holder 66 and is positioned within the knife slot 60 of the cartridge body 50 such that movement of the knife holder 66 from its retracted position to its advanced position (FIG. 10) advances the knife blade 64 through the cartridge body 50 and into engagement with the anvil assembly 22.

FIG. 2 illustrates a distal end portion of the stapling device 10 which includes the thrust bar 32 that is positioned within the distal support portion 46 of the clamp slide assembly 30. The thrust bar 32 has a proximal end (not shown) that is coupled to the trigger 20. The knife holder 66 is coupled to the thrust bar (not shown) when the cartridge assembly 20 is loaded onto the stapling device 10. When the trigger 20 is actuated to move the thrust bar 32 between retracted and advanced positions, the knife holder 66 is advanced from its retracted position to its advanced position within the cartridge body 50. As the knife holder 66 is advanced from its retracted position towards its advanced position, the knife holder 56 abuts and advances the staple pusher 52 from its retracted to its advanced position. For a more detailed description of a stapling device including a thrust bar, see the '508 patent.

Figure 4:
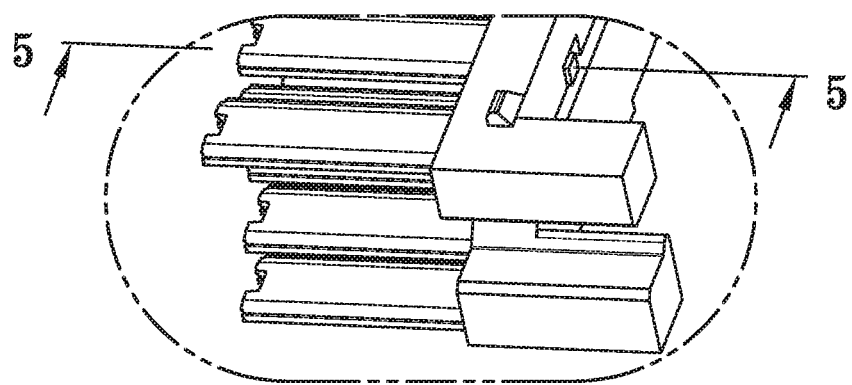
FIG. 4 is an enlarged view of the indicated area of detail shown in FIG. 3.
Figure 5:
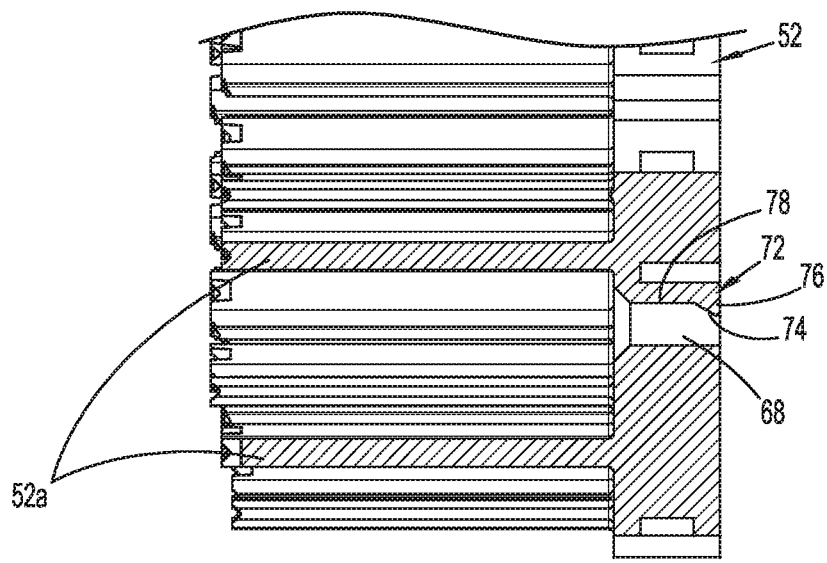
FIG. 5 is a cross-sectional view taken along section lines 5-5 of FIG. 4.
Figure 6:
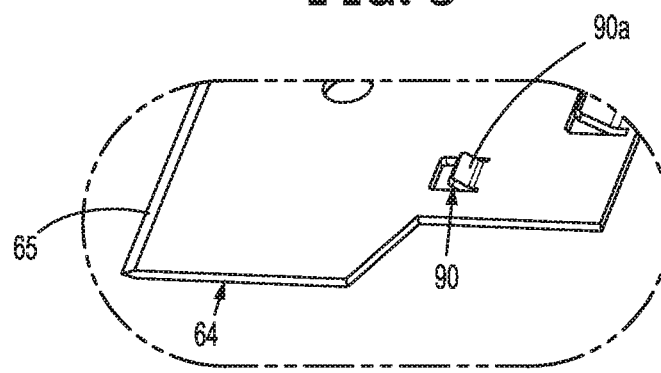
FIG. 6 is an enlarged view of the indicated area of detail shown in FIG. 3.

FIGS. 3-8 illustrate the locking device of the staple pusher 52, the knife holder 66, and the knife blade 64. FIGS. 3-5 illustrate the staple pusher 52 which includes a staple pusher body 70 that defines the knife slot 60 in the staple pusher 52. The staple pusher body 70 includes a first part of the locking device including a stop member 72 that extends into the knife slot 68. In certain aspects of the disclosure, the stop member 72 includes a tapered distal face 74 and a stop surface 76 that extends in a direction transverse to the longitudinal axis "Y" of the stapling device 10 (FIG. 1). The stop member 72 can be formed from a resilient material that allows the stop member 72 to be deformed outwardly of the knife blade 64 as described below. Alternately, the stop member 72 can be supported on a cantilevered arm 78 that facilitates movement of the stop member 72 to a position outwardly of the knife blade 64.

The knife blade 64 has a curvature that corresponds to the curvature of the cartridge body 50 and includes a proximal portion 64a and a distal portion 64b. It is envisioned that aspects of the disclosure are suitable for use in linear, curved, or angled cartridge assemblies. The distal portion 64b of the knife blade 64 defines a cutting edge 65. The proximal portion 64a of the knife blade 64 is fixedly received within a groove 80 (FIG. 8) that is defined within a distal face of the knife holder 66 and includes securement tabs 82 (FIG. 3). The securement tabs 82 project outwardly from an outer surface of the knife blade 68 at an angle to facilitate insertion of the knife blade 64 into the groove 80 of the knife holder 66 but to prevent removal of the knife blade 64 from the groove 80. The knife blade 64 includes a second part of the locking device including a locking projection 90 that is aligned with and positioned distally of the stop member 72 of the staple pusher 52 when the staple pusher 52 and the knife holder 66 are in their retracted positions. The locking projection 90 can be in the form of a tab that extends from the knife blade 64 and includes a tapered proximal face 90a that is aligned with the tapered distal face 74 of the stop member 72. Other locking projection configurations are envisioned.

FIGS. 7 and 8 illustrate the stapling device 10 (FIG. 1) in a pre-fired position with the staple pusher 52 and the knife holder 66 in their retracted positions. In this position, the knife blade 64 extends through the knife slot 68 of the staple pusher 52 into the knife slot 60 of the staple cartridge 50 and the cutting edge 65 of the knife blade 64 is shielded within the cartridge body 50 of the cartridge assembly 20. The locking projection 90 of the knife blade 64 is positioned distally of the stop member 72 of the staple pusher 52 with the tapered proximal face 90a of the locking projection 90 in spaced alignment with the tapered distal face 74 of the stop member 72.

FIGS. 9 and 10 illustrate the stapling device 10 (FIG. 1) as the stapling device 10 moves toward the fired position with the staple pusher 52 and the knife holder 66 moving to their advanced positions in the direction indicated by arrow "A" in FIG. 10. For a detailed description of the operation of the handle assembly 12 to effect approximation and firing the stapling device 10, see the '508 patent. In the fired position, the thrust bar 32 is advanced to advance the knife holder 66 to its advanced position. The knife holder 66 is in abutting relation to the staple pusher 52. As such, the staple pusher 52 moves to its advanced position in response to movement of the knife holder 66 to its advanced position. When the staple pusher 52 moves to its advanced position, the fingers 52a of the staple pusher 52 move through the staple pockets 58 of the cartridge body 50 to eject the staples 62 from within the staple pockets 58 into the anvil assembly 22. When the knife holder 66 is moved to its advanced position, the knife blade 64 which is fixedly supported on the knife holder 66 is advanced within the cartridge body 50 to move the cutting edge 65 of the knife blade 64 into engagement with the anvil assembly 22. In the advanced positions of the staple pusher 52 and the knife holder 66, the locking projection 90 of the knife blade 64 remains in a position located distally of the stop member 72 of the staple pusher 52 with the tapered proximal face 90a of the locking projection 90 in spaced alignment with the tapered distal face 74 of the stop member 72.

Figure 11:
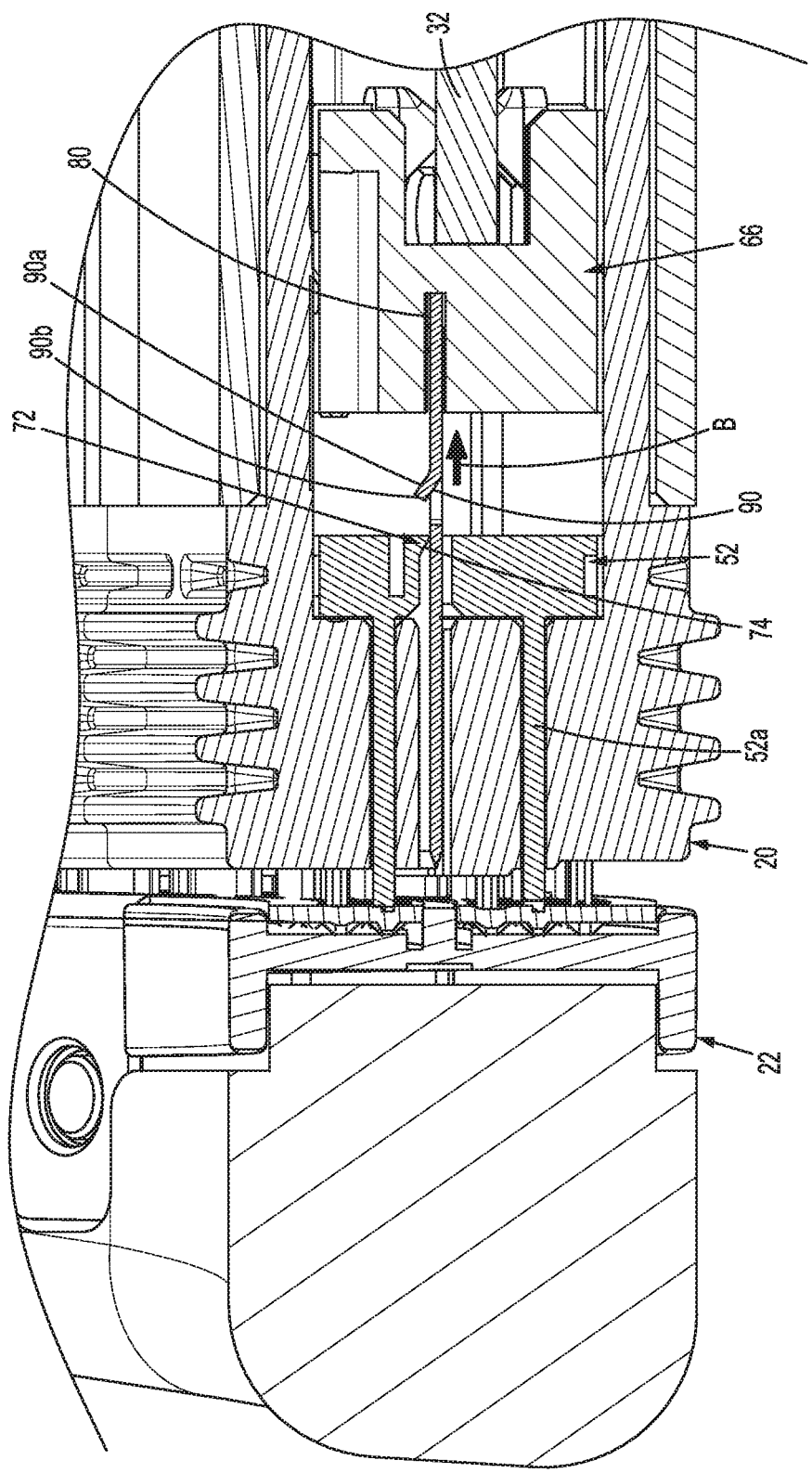
FIG. 11 is a side perspective view of the stapling device shown in FIG. 1 in the clamped and fired position with the knife assembly in a retracted position.

FIG. 11 illustrates the stapling device 10 (FIG. 1) in a post-fired position as the knife holder 66 is moved to its retracted position in the direction indicated by arrow "B" in FIG. 10. As described above, the staple pusher 52 and the knife holder 66 are in abutting relation. As such, when the knife holder 66 is moved towards its retracted position via movement of the thrust bar 32 to its retracted position, the knife holder 66 moves independently of the staple pusher 52 which remains in its advanced position. As the knife holder 66 moves in relation to the staple pusher 52, the knife blade 64 is withdrawn from the knife slot 68 formed in the staple pusher 52. As the knife blade 64 moves proximally through the knife slot 68, the tapered proximal face 90a of the locking projection 90 engages the tapered distal face 74 of the stop member 72 to deform the stop member 72 outwardly of the knife blade 64. This allows the locking projection 90 of the knife blade 64 to move to a position proximal of the stop member 72. In this position, the locked position, a distal edge 90b of the locking projection 90 of the knife blade 64 is positioned proximally of and in alignment with the orthogonal stop surface 76 of the stop member 72.

In the locked position, movement of the knife holder 66 and knife blade 64 back to their advanced positions is obstructed by engagement between the locking projection 90 of the knife blade 64 and the stop member 72 of the staple pusher 52. This retains the knife holder 66 and the knife blade 64 in substantially retracted positions to retain the cutting edge 65 of the knife blade 64 shielded within the cartridge body 52 to minimize any likelihood of injury to a clinician.

FIGS. 12-16 illustrate a cartridge assembly shown generally as cartridge assembly 120 having additional aspects of the disclosure. The cartridge assembly 120 is similar to cartridge assembly 20 in construction and operation but includes a different locking device as described below. The cartridge assembly 120 includes a cartridge body 150, a staple pusher 152, a knife blade 164, and a knife holder 166 that are substantially as described above in regard to the cartridge assembly 20. In cartridge assembly 120, the locking device including the stop member 72 and the locking projection 90 have been replaced with a stop member 172 and a locking projection 190. The stop member 172 is formed on the knife holder 166 and includes an angled wall 174 and a stop surface 176 that is substantially perpendicular to the longitudinal axis "Y" (FIG. 1) of the stapling device 10 (FIG. 1). The locking projection 190 includes a resilient leaf spring 192 (FIG. 13) that has a proximal end 192a and a distal end 192b. The distal end 192b is secured to a post 194 that is formed on the staple pusher 152 and is biased in a direction indicated by arrow "D" in FIG. 13.

Figure 12:
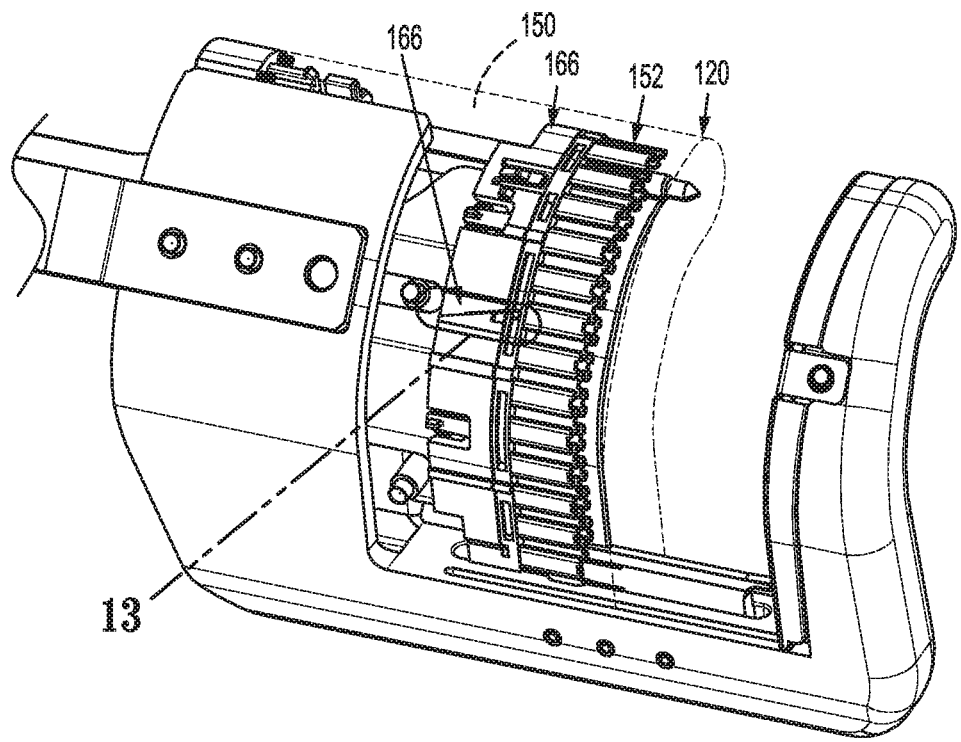
FIG. 12 is a side perspective view of a distal portion of the stapling device shown in FIG. 1 including an alternative cartridge assembly including additional aspects of the disclosure with the stapling in a pre-fired, unclamped position.
Figure 13:
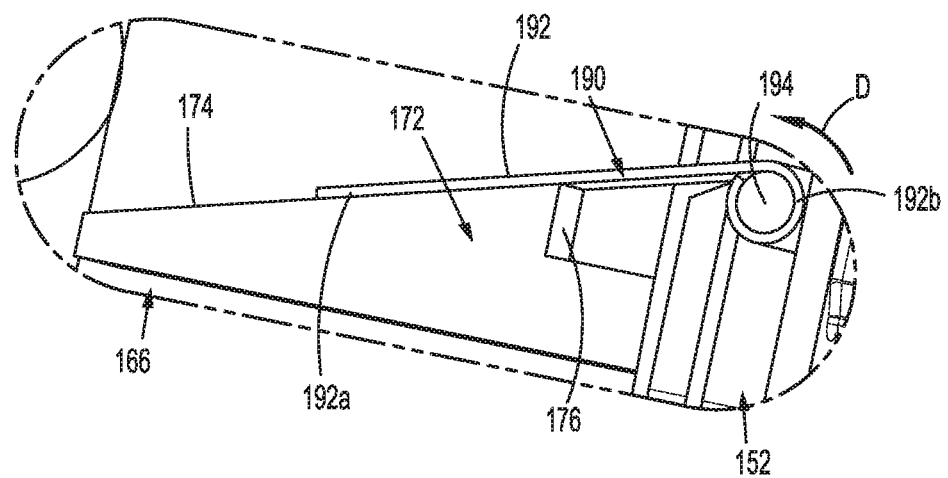
FIG. 13 is an enlarged view of the indicated area of detail shown in FIG. 12.
Figure 14:
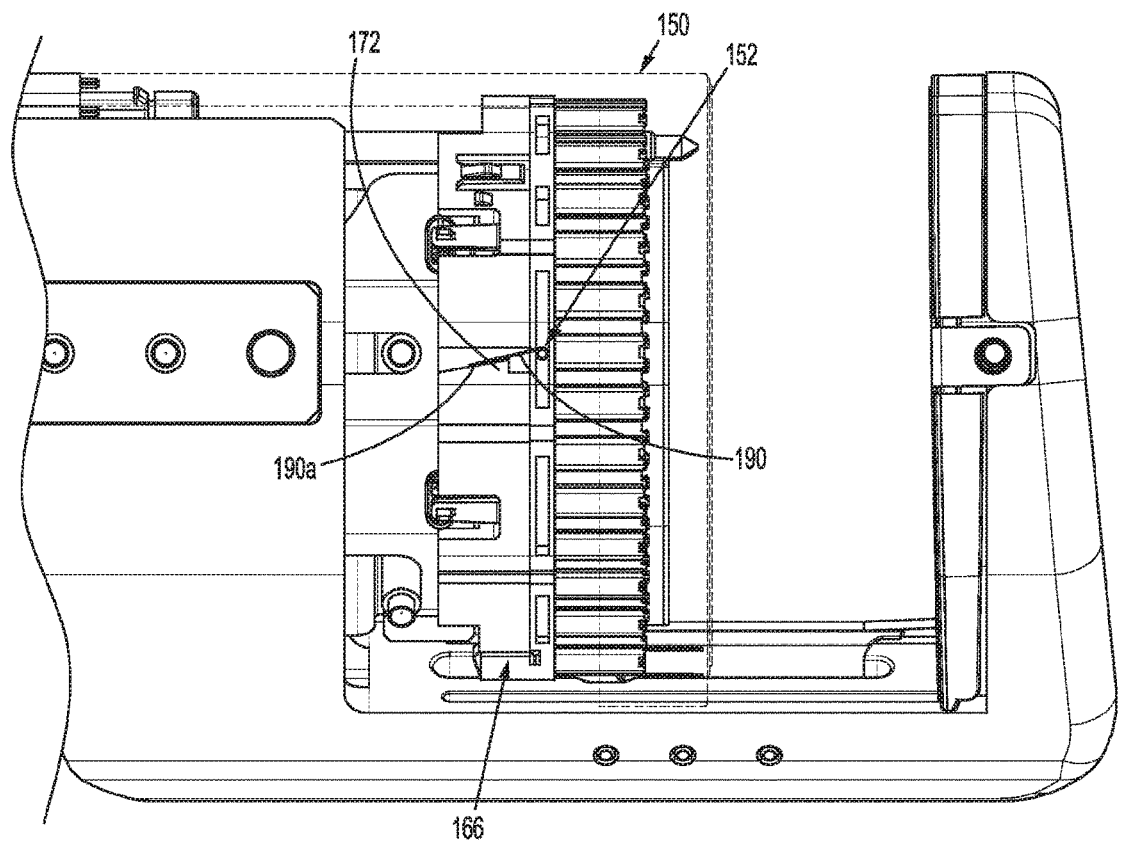
FIG. 14 is a side perspective view of the distal portion of the stapling device shown in FIG. 12 with the stapling in the pre-fired, unclamped position.
Figure 15:
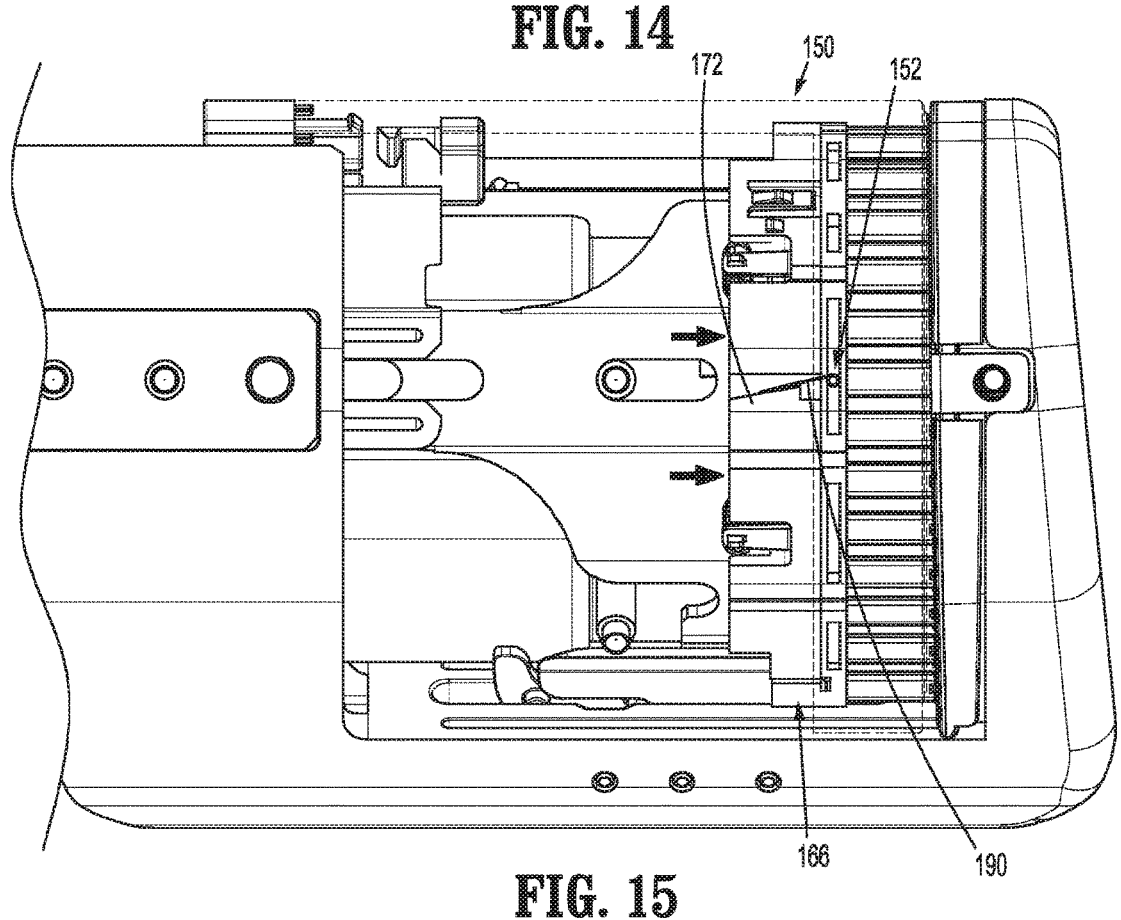
FIG. 15 is a side perspective view of the distal portion of the stapling device shown in FIG. 12 with the stapling device in the clamped and fired position with the knife assembly in an advanced position.

When the stapling device 10 (FIG. 1) is in a pre-fired position as illustrated in FIGS. 12-14, the staple pusher 152, the knife holder 166, and the knife blade 164 are in their retracted positions. In this position, the leaf spring 192 is positioned on the angled wall 174 (FIG. 13) of the stop member 172 with the proximal end 192a of the leaf spring 192 positioned proximally of the stop surface 176. As illustrated in FIG. 15, the leaf spring 192 remains in this position in relation to the stop member 172 when the stapling device 10 is fired and the staple pusher 152, the knife holder 166, and the knife blade 164 are moved to their advanced positions.

Figure 16:
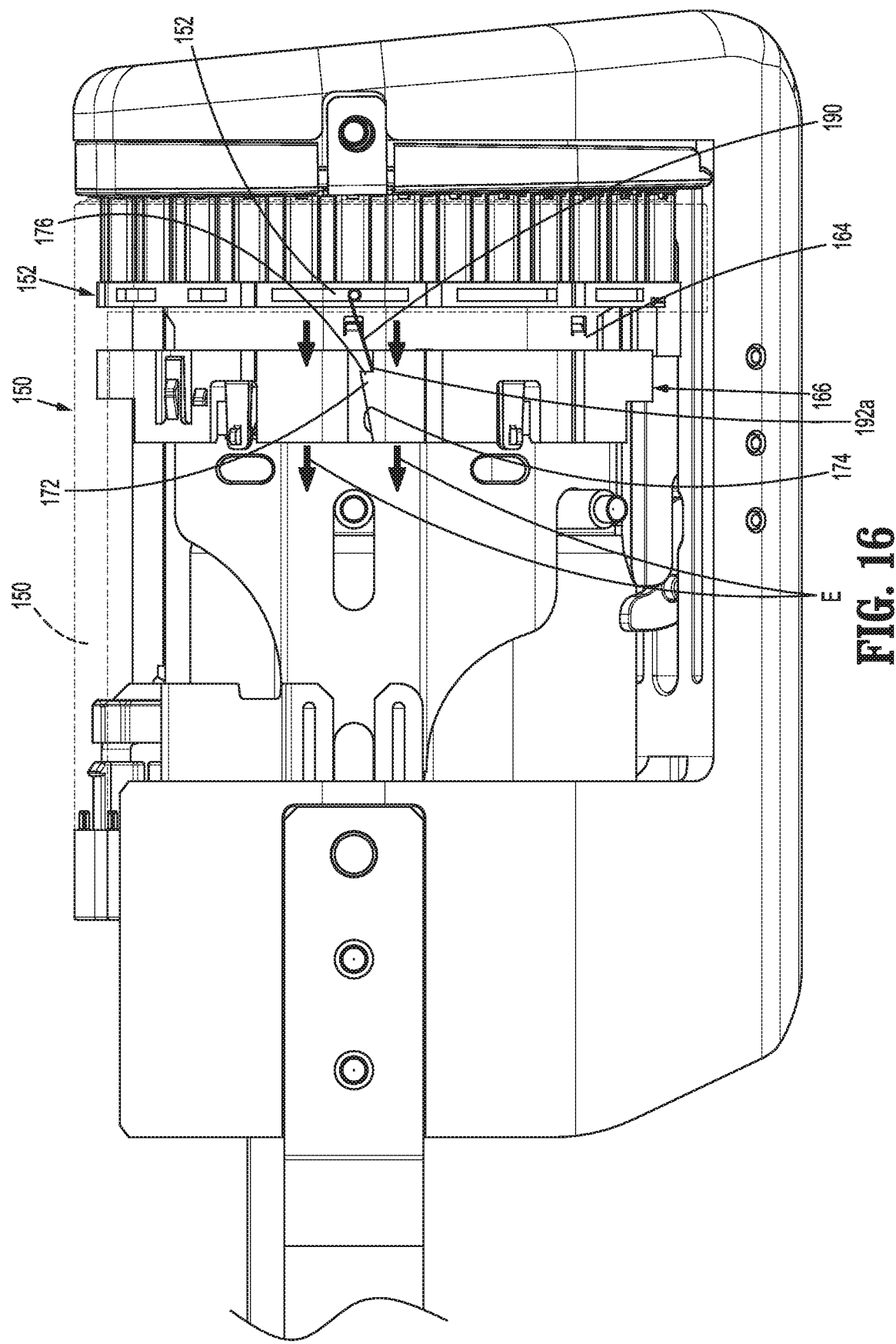
FIG. 16 is a side perspective view of the distal portion of the stapling device shown in FIG. 12 with the stapling in the clamped and fired position and the knife assembly in a fully retracted position.

After the stapling device 10 is fired and the knife holder 166 is returned to its retracted position independently of the staple pusher 152 in the direction indicated by arrows "E" in FIG. 16, the stop member 172 moves proximally with the knife holder 166 in relation to the leaf spring 192 such that the proximal end 192a (FIG. 16) of the leaf spring 192 moves to a locked position distally of the stop surface 176 of the stop member 172. The resilience of the leaf spring 192 moves the proximal end 192a of the leaf spring 192 off of the wall 174 into alignment with the stop surface 176. In the locked position, movement of the knife holder 166 and knife blade 164 back to their advanced positions is obstructed by engagement between the proximal end 192a of the leaf spring 190 which is supported on the staple pusher 152 and the stop surface 176 of the stop member 172 of the knife holder 166. This retains the knife holder 166 and the knife blade 164 in substantially retracted positions to retain the cutting edge 165 of the knife blade 164 shielded within the cartridge body 150 to minimize any likelihood that the cutting edge 165 of the knife blade 164 will move to a position extending from the cartridge body 150 and endanger a clinician.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of advantages of the disclosure based on the above-described aspects of the disclosure. As well, one skilled in the art will appreciate further features and disclosure. Accordingly, the disclosure is not to be limited by what has been particularly shown and described, except as indicated by the appended claims.

What is claimed is:

1. A stapling device comprising:
a handle assembly including a stationary handle and a trigger that is movable in relation to the stationary handle;
an elongate body extending distally from the handle assembly and defining a longitudinal axis, the elongate body having a distal portion and a proximal portion;
an approximation assembly extending from the handle assembly along the elongate body, the approximation assembly including a clamp slide assembly having a distal support portion, the clamp slide assembly being movable along the elongate body between retracted and advanced positions;
a tool assembly supported on the distal portion of the elongate body, the tool assembly including an anvil assembly and a cartridge assembly, the cartridge assembly releasably supported on the distal support portion of the clamp slide assembly and movable in relation to the anvil assembly between spaced and clamped positions in response to movement of the clamp slide assembly between the retracted and advanced positions, the cartridge assembly including a cartridge body, a knife assembly, and a staple pusher, the knife assembly positioned within the cartridge body at a position proximally of the staple pusher and movable between retracted and advanced positions in response to actuation of the handle assembly, the staple pusher positioned within the staple cartridge distally of the knife assembly such that movement of the knife assembly from its retracted position to its advanced position moves the staple pusher from its retracted position to its advanced position; and
a locking device supported on the cartridge assembly, the locking device including a stop member supported on one of the knife assembly and the staple pusher and a locking projection supported on the other of the knife assembly and the staple pusher, the locking projection being movable in response to movement of the knife assembly from its advanced position back to its retracted position from a first position facilitating advancement of the knife assembly to a second position obstructing advancement of the knife assembly.

2. The stapling device of claim 1, wherein the knife assembly includes a knife blade and a knife holder, the knife blade secured to the knife holder and defining a cutting edge.

3. The stapling device of claim 1, wherein the cartridge assembly and the anvil assembly define axes transverse to the longitudinal axis of the elongate body.

4. The stapling device of claim 3, wherein the cartridge assembly and the anvil assembly are curved along their longitudinal axes.

5. The stapling device of claim 2, wherein the staple pusher defines a knife slot and the knife blade is movably positioned within the knife slot.

6. The stapling device of claim 5, wherein the stop member is formed on the staple pusher and the locking projection is formed on the knife blade, the locking projection extending into the knife slot of the staple pusher.

7. The stapling device of claim 4, wherein the stop member includes a tapered distal face and a proximally facing stop surface that extends in a direction transverse to the longitudinal axis of the elongate body, the stop member being deformable from an undeformed condition to a deformed condition upon engagement with the locking projection to facilitate movement of the locking projection from a position distally of the stop surface to a position proximally of the stop surface.

8. The stapling device of claim 7, wherein the locking projection includes a tab extending from the knife blade, the tab aligned with the stop member within the knife slot.

9. The stapling device of claim 8, wherein the locking projection includes a tapered proximal face that is aligned with the tapered distal face of the stop member when the staple pusher and the knife assembly are in their retracted positions.

10. The stapling device of claim 1, wherein the stop member is formed on the knife holder of the knife assembly and the locking projection is formed on the staple pusher.

11. The stapling device of claim 10, wherein the stop member is formed on the knife holder of the knife assembly and includes a proximally facing angled wall and a distally facing stop surface, the distally facing stop surface extending in a direction perpendicular to the longitudinal axis of the elongate body.

12. The stapling device of claim 11, wherein the locking projection includes a resilient leaf spring supported on the staple pusher, the resilient leaf spring having a proximal end and being movable from a deformed condition to a non-deformed condition in response to movement of the knife assembly from its advanced position to its retracted position.

13. The stapling device of claim 12, wherein when the staple pusher and the knife assembly are in their retracted positions, the resilient leaf spring is positioned on the angled wall of the stop member in the deformed condition with the proximal end of the resilient leaf spring positioned proximally of the stop surface.

14. The stapling device of claim 12, wherein when the knife assembly is in its retracted position and the staple pusher is in its advanced position, the proximal end of the resilient leaf spring is positioned distally of the stop surface.

15. A cartridge assembly comprising:
a cartridge body;
a knife assembly positioned within the cartridge body, the knife assembly movable between retracted and advanced positions; and
a staple pusher positioned within the cartridge body distally of the knife assembly such that movement of the knife assembly from its retracted position to its advanced position moves the staple pusher from a retracted position to an advanced position; and a locking device including a stop member supported on one of the knife assembly and the staple pusher and a locking projection supported on the other of the knife assembly and the staple pusher, the locking projection movable in response to movement of the knife assembly from its advanced position back to its retracted position from a first position facilitating advancement of the knife assembly to a second position obstructing advancement of the knife assembly.

16. The cartridge assembly of claim 15, wherein the knife assembly includes a knife holder and a knife blade secured to the knife holder and the staple pusher defines a knife slot, the knife blade being movably positioned within the knife slot and defining a cutting edge.

17. The cartridge assembly of claim 16, wherein the stop member is formed on the staple pusher and the locking projection is formed on the knife blade, the locking member extending into the knife slot of the staple pusher.

18. The cartridge assembly of claim 17, wherein the stop member includes a tapered distal face and a proximally facing stop surface that extends in a direction transverse to the longitudinal axis of the elongate body, the stop member being deformable from an undeformed condition to a deformed condition upon engagement with the locking projection to facilitate movement of the locking projection from a position distal of the stop surface to a position proximal of the stop surface.

19. The cartridge assembly of claim 18, wherein the locking projection includes a tab extending from the knife blade, the locking projection having a tapered proximal face that is aligned with the tapered distal face of the stop member when the staple pusher and the knife assembly are in their retracted positions.

20. The cartridge assembly of claim 16, wherein the stop member is formed on the knife holder of the knife assembly and the locking projection is formed on the staple pusher, the stop member including a proximally facing angled wall and a distally facing stop surface.

21. The stapling device of claim 20, wherein the locking projection includes a resilient leaf spring supported on the staple pusher, the resilient leaf spring having a proximal end and being movable from a deformed condition to a non-deformed condition in response to movement of the knife assembly from its advanced position to its retracted position.

22. The cartridge assembly of claim 21, wherein when the staple pusher and the knife assembly are in their retracted positions, the resilient leaf spring is positioned on the angled wall of the stop member in the deformed condition with the proximal end of the resilient leaf spring positioned proximally of the stop surface, and when the knife assembly is in its retracted position and the staple pusher is in its advanced position, the proximal end of the resilient leaf spring is positioned distally of the stop surface to obstruct advancement of the assembly.

* * * * *